United States Patent [19]
Fernald et al.

[11] Patent Number: 6,093,285
[45] Date of Patent: Jul. 25, 2000

[54] PURIFICATION OF 1,3-BUTADIENE

[75] Inventors: Daniel T. Fernald; Stephen L. Ege; Si M. Nguyen, all of Houston; Richard Peacock, Missouri City, all of Tex.; Larry L. Nash; George A. Moczygemba, both of Bartlesville, Okla.

[73] Assignee: Phillips Petroleum Company, Bartlesville, Okla.

[21] Appl. No.: 09/144,117

[22] Filed: Aug. 31, 1998

[51] Int. Cl.$^7$ .............................. B01D 3/00; C07C 7/04; C07C 51/44

[52] U.S. Cl. .............................. 203/14; 203/87; 203/98; 203/99; 203/DIG. 19; 585/810

[58] Field of Search .................... 203/8, 14, 99, 203/98, DIG. 19, 86, 41, 87, 94, 18, DIG. 9; 202/204, 158, 182, 186; 34/391, 468; 585/810

[56] References Cited

U.S. PATENT DOCUMENTS

| | | | |
|---|---|---|---|
| 3,281,489 | 10/1966 | Goering | 260/681.5 |
| 3,620,930 | 11/1971 | Tschopp et al. | 203/87 |
| 4,339,623 | 7/1982 | Morgan et al. | 585/867 |
| 5,397,439 | 3/1995 | Kandori et al. | 568/913 |

*Primary Examiner*—Virginia Manoharan
*Attorney, Agent, or Firm*—Jeffrey R. Anderson

[57] ABSTRACT

A system and process for purifying a 1,3-butadiene feedstock containing 1,3-butadiene and various impurities by first introducing the 1,3-butadiene feedstock stream to a separation column to produce an intermediate product stream containing 1,3-butadiene and residual impurities and then introducing the produced intermediate product stream through a condenser to a suitable dryer for removing residual impurities from the intermediate product stream and thereby forming a purified 1,3-butadiene stream. The separation column separates an overhead stream, containing 1,3-butadiene and impurities such as propadiene, water and oxygen, and a bottoms stream, containing impurities such as polymerization inhibitor, ethyl acetylene, 1,3-butadiene dimer, pentane and 1,2-butadiene, from the intermediate product stream which leaves the separation column in the form of a vapor side draw stream.

10 Claims, 2 Drawing Sheets

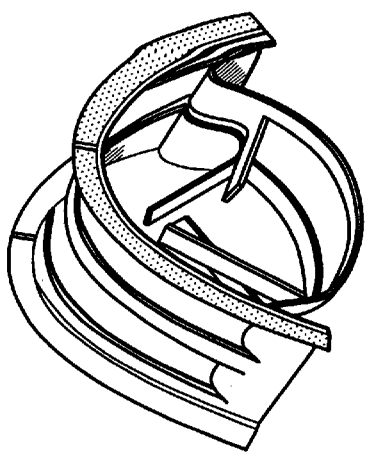
FIG. 2(c)
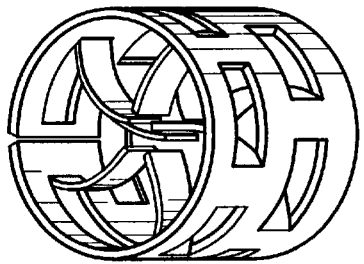
FIG. 2(f)
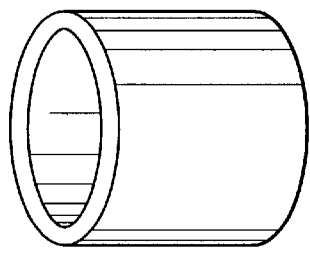
FIG. 2(b)
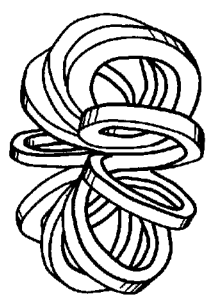
FIG. 2(e)
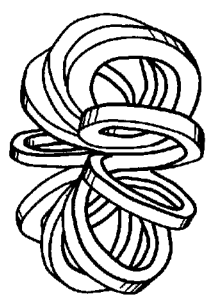
FIG. 2(a)
FIG. 2(d)

PURIFICATION OF 1,3-BUTADIENE

The present invention relates to the field of hydrocarbon purification. In another aspect, the invention relates to a process for the purification of a 1,3-butadiene feedstock. In yet another aspect, the invention relates to an apparatus for purifying a 1,3-butadiene feedstock.

BACKGROUND OF THE INVENTION

It is well known in the art to use 1,3-butadiene as a feedstock in processes for the production of polymer compounds, such as styrene/butadiene copolymer resins. One of the problems encountered in these processes is that the polymerization catalysts employed are sensitive to oxygen, moisture and other impurities including polymerization inhibitor. Typical purification schemes used today include a two-step fractionation scheme and a fixed bed desiccant dryer scheme. In the two-step fractionation scheme water and oxygen are eliminated out the top of the first fractionator and heavier impurities and polymerization inhibitor are removed from the bottom of the second fractionator. The problems encountered in this prior art two-step fractionation system include unwanted polymerization in and around the first fractionator and the expense of constructing and operating two columns. A drawback of the prior art desiccant dryer scheme is that high amounts of 1,3-butadiene dimer, and other heavies, can pass through the dryers and on to the polymerization reactor. Therefore, development of a more efficient process for purifying 1,3-butadiene without the problem of unwanted polymerization in and around the purification equipment would be a significant contribution to the art.

BRIEF SUMMARY OF THE INVENTION

It is, thus, an object of the present invention to provide an improved process for purifying a 1,3-butadiene feedstock which is economical and efficient.

A further object of the present invention is to provide an improved system to be used in purifying a 1,3-butadiene feedstock which is economical in construction and reliable and efficient in operation.

In accordance with the present invention, a process is provided for purifying a 1,3-butadiene feedstock. The process includes the steps of:

separating a 1,3-butadiene feedstock into an overhead stream comprising water, a bottoms stream comprising at least one heavy impurity and a polymerization inhibitor, and a vapor side draw stream comprising 1,3-butadiene and residual impurities;

condensing the vapor side draw stream to form an intermediate product stream; and removing at least a portion of the residual impurities from the intermediate product stream to form a purified 1,3-butadiene stream.

In accordance with another aspect of the present invention a system or apparatus is provided for purifying a 1,3-butadiene feedstock comprising:

a separation column, defining a separation zone having an upper portion, a medial portion and a lower portion, for separating the 1,3-butadiene feedstock into an overhead stream comprising water, a bottoms stream comprising at least one heavy impurity and a polymerization inhibitor, and a vapor side draw stream comprising 1,3-butadiene and residual impurities;

means for connecting the separation zone in fluid flow communication with a source of 1,3-butadiene;

first condensing means in fluid flow communication with the medial portion of the separation column for condensing the vapor side draw stream to form an intermediate product stream comprising 1,3-butadiene and residual impurities; and means in fluid flow communication with the first condensing means for removing at least a portion of the residual impurities from the intermediate product stream to form a purified 1,3-butadiene stream.

Other objects and advantages of the invention will be apparent from the detailed description of the invention and the appended claims.

BRIEF DESCRIPTION OF THE DRAWINGS

FIGS. 2 (a)–(f) are perspective views each illustrating an alternative configuration of packing elements useful in the present invention.

DETAILED DESCRIPTION OF THE INVENTION

Figure 1:
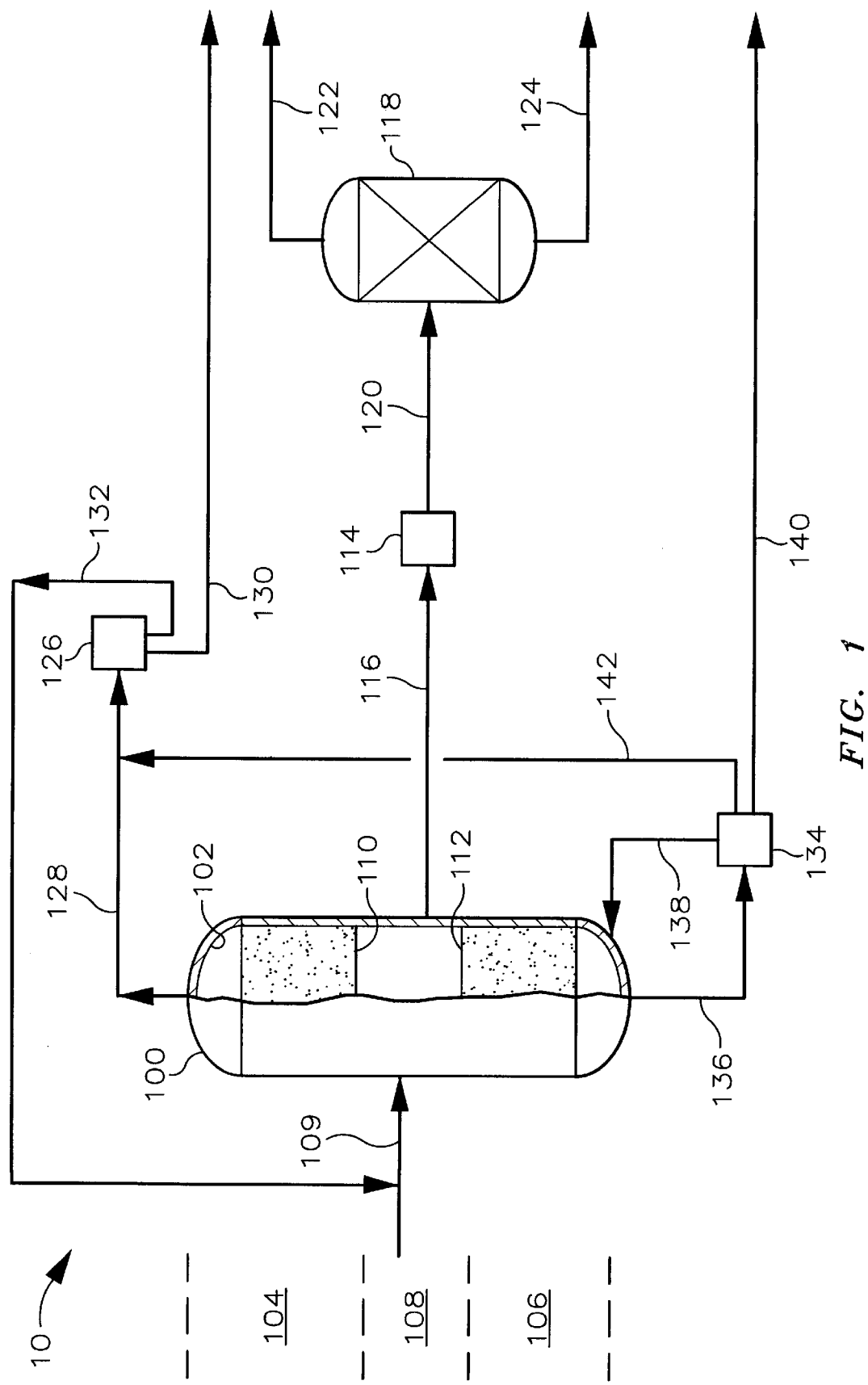
FIG. 1 is a partially cut-away elevation of a purification system representing an embodiment of the present invention.

The process of this invention involves the purification of a 1,3-butadiene feedstock.

The 1,3-butadiene feedstock comprises 1,3-butadiene and impurities. The impurities can comprise oxygen and/or water and/or propadiene and/or methanol and/or peroxide ($H_2O_2$) and/or hydrogen sulfide and/or a polymerization inhibitor and/or at least one heavy impurity. The polymerization inhibitor can be any compound effective in inhibiting the autopolymerization of 1,3-butadiene. The polymerization inhibitor can comprise a phenolic hydrocarbon. The most typical polymerization inhibitor used with 1,3-butadiene is tert-butyl catechol.

The at least one heavy impurity can be any hydrocarbon which is normally present with 1,3-butadiene in solution in a 1,3-butadiene storage tank. More particularly, the at least one heavy impurity can comprise a hydrocarbon compound selected from the group consisting of ethyl acetylene, 1,3-butadiene dimer, pentane, 1,2-butadiene, vinyl acetylene, methyl acetylene, acetaldehyde and diethylhydroxylamine.

The concentration of impurities in the 1,3-butadiene feedstock is typically in the range of from about 100 parts per million by weight ("ppmw") to about 1000 ppmw, more typically in the range of from about 150 ppmw to about 800 ppmw, and most typically from 150 ppmw to 500 ppmw.

In the present invention, the 1,3-butadiene feedstock is charged to a separation column, defining a separation zone, for separation into an overhead stream comprising 1,3-butadiene, propadiene, water, peroxide, methanol, hydrogen sulfide and oxygen, a bottoms stream comprising at least one heavy impurity and a polymerization inhibitor, and a vapor side draw stream comprising 1,3-butadiene and residual impurities which can include methanol, vinyl acetylene, propadiene, methyl acetylene, ethyl acetylene, pentane, 1,3-butadiene dimer, water, oxygen, 1,2-butadiene, acetaldehyde, hydrogen sulfide, peroxide, diethylhydroxylamine and polymerization inhibitor. The separation zone comprises an upper portion further comprising a first packed bed effective in separating water from 1,3-butadiene, a lower portion further comprising a second packed bed effective in separating the at least one heavy impurity and the polymerization inhibitor from 1,3-butadiene, and a medial portion. The packed beds can comprise packing elements selected from the group consisting of raschig rings, berl saddles, metal Intalox® saddles, ceramic Intalox® saddles, Tellerette® packing elements, Pall-Ring® filler bodies and combinations of any two or more thereof.

The temperature of the 1,3-butadiene feedstock charged to the separation zone can be in the range of from about 20° C. to about 50° C., preferably in the range of from about 25° C. to about 45° C., and most preferably from 30° C. to 40° C.

The separation zone can be operated at a pressure in the range of from about 0 psia to about 200 psia, preferably in the range of from about 20 psia to about 170 psia, and most preferably from 50 psia to 130 psia.

The temperature of the vapor side draw stream removed from the separation zone can be in the range of from about 40° C. to about 50° C., preferably in the range of from about 40° C. to about 48° C., and most preferably from 40° C. to 45° C.

The vapor side draw stream more particularly comprises residual impurities in the range of from about 21 ppmw to about 50 ppmw, preferably in the range of from about 21 ppmw to about 40 ppmw, and most preferably from 21 ppmw to 30 ppmw. The vapor side draw stream is condensed in a condenser operated under conditions suitable for producing a liquid intermediate product stream. The intermediate product stream can then be charged to means for removing residual impurities present in the intermediate product stream forming a purified 1,3-butadiene stream and a residual impurities stream. The means for removing residual impurities can consist of any suitable apparatus effective in removing the residual impurities. Suitable means for removing residual impurities can consist of a dryer, an indirect heat dryer and a coalescer. The presently preferred means for removing is a desiccant dryer comprising desiccant.

The purified 1,3-butadiene stream comprises impurities in the range of from about 0 ppmw to about 20 ppmw, preferably in the range of from about 0 ppmw to about 19 ppmw, and most preferably from 0 ppmw to 18 ppmw.

In another embodiment, at least a portion of the overhead stream can be condensed producing a water phase stream comprising water and a hydrocarbon phase stream comprising 1,3-butadiene and some impurities. The hydrocarbon phase stream is then refluxed to the separation zone. Condensing and refluxing at least a portion of the overhead stream results in increased 1,3-butadiene purification efficiency.

In still another embodiment, at least a portion of the bottoms stream can be reboiled to form a boil-up vapor stream comprising 1,3-butadiene and a bottoms residue stream comprising 1,3-butadiene, at least one heavy impurity and a polymerization inhibitor. The boil-up vapor stream is returned to the lower portion of the separation zone. Reboiling and returning at least a portion of the bottoms stream to the separation zone increases the efficiency of the 1,3-butadiene purification process.

In yet another embodiment, a slip stream of the bottoms residue stream can be charged into the overhead stream prior to condensing at least a portion of the overhead stream. The charging of a slip stream of the bottoms residue stream, which comprises a polymerization inhibitor, minimizes the production of unwanted polymer in and around the equipment used in condensing and refluxing at least a portion of the overhead stream.

The purification system of the present invention will be described with reference to the drawings. Reference to the specific configurations of the drawings is not meant to limit the invention to the details of the drawings disclosed in conjunction therewith.

Referring to FIG. 1, therein is illustrated the inventive purification system or apparatus 10 including a separation column 100 having an inside wall 102 which defines a separation zone including an upper portion 104, a lower portion 106, and a medial portion 108 between the upper portion 104 and the lower portion 106. The separation column 100 is connected in fluid flow communication with a conduit 109 for introducing a 1,3-butadiene feedstock into the separation zone. The separation column 100 provides means for separating a 1,3-butadiene feedstock into an overhead stream comprising water, a bottoms stream comprising at least one heavy impurity and a polymerization inhibitor, and a vapor side draw stream comprising 1,3-butadiene and residual impurities.

The upper portion 104 of the separation zone further includes a first packed bed 110 and the lower portion 106 of the separation zone further includes a second packed bed 112.

The medial portion 108 of the separation zone is connected in fluid flow communication via conduit 116 with a first condenser 114 providing first condensing means for condensing the vapor side draw stream to form an intermediate product stream. The first condenser 114 is connected in fluid flow communication via conduit 120 with a dryer 118 providing dryer means for removing residual impurities from the intermediate product stream. The apparatus 10 further includes a conduit 122 in fluid flow communication with the dryer 118 for removing a purified 1,3-butadiene stream from the dryer 118 and a conduit 124 in fluid flow communication with the dryer 118 for removing a residual impurities stream from the dryer 118.

The upper portion 104 of the separation zone is connected in fluid flow communication via conduit 128 with a second condenser 126 providing second condensing means for condensing at least a portion of an overhead stream. The second condenser 126 is in fluid flow communication with a conduit 130 which provides means for removing a water phase stream and a conduit 132 which provides means for removing a hydrocarbon phase stream for reflux to the separation zone.

The lower portion 106 of the separation zone is connected in fluid flow communication via conduit 136 with a reboiler 134. The reboiler 134 is connected in fluid flow communication via conduit 138 to the lower portion 106 of the separation zone and provides reboiler means for forming and returning a boil-up vapor stream to the lower portion 106 of the separation zone. The reboiler 134 is further connected in fluid flow communication to a conduit 140 which provides means for removing a bottoms residue stream from said reboiler 134. A conduit 142 is connected in fluid flow communication with conduit 128 and conduit 140 and provides means for introducing a slip stream of the bottoms residue stream from conduit 140 into conduit 128.

The first packed bed 110 comprises a plurality of packing elements suitable for use under the separation conditions disclosed herein, and preferably selected from the group consisting of raschig rings, berl saddles, metal Intalox® saddles, ceramic Intalox® saddles, Tellerette® packing elements, Pall-Ring® filler bodies, and combinations of any two or more thereof.

The second packed bed 112 comprises a plurality of packing elements suitable for use under the separation conditions disclosed herein, and preferably selected from the group consisting of raschig rings, berl saddles, metal Intalox® saddles, ceramic Intalox® saddles, Tellerette® packing elements, Pall-Ring® filler bodies, and combinations of any two or more thereof.

FIG. 2(a) illustrates the configuration of a typical raschig ring packing element. FIG. 2(b) illustrates the configuration of a typical berl saddle packing element. FIG. 2(c) illustrates the configuration of a typical metal Intalox® saddle packing element. FIG. 2(d) illustrates the configuration of a typical ceramic Intalox® saddle packing element. FIG. 2(e) illustrates the configuration of a typical Tellerette® packing element. FIG. 2(f) illustrates the configuration of a typical Pall-Ring® filler body.

The following example is provided to further illustrate this invention and is not to be considered as unduly limiting the scope of this invention.

Calculated Example

This example illustrates the purification of a 1,3-butadiene feedstock using the inventive purification system.

A computer model was used to simulate the purification of a 1,3-butadiene feedstock and calculate the compositions of the intermediate product stream and the purified 1,3-butadiene stream produced by the operation of the inventive 1,3-butadiene purification system. The 1,3-butadiene feedstock composition used as an input to the computer model was obtained from an analysis of a 1,3-butadiene sample taken from a 1,3-butadiene storage tank at a chemical plant.

A 1,3-butadiene feedstock stream is introduced into the inventive separation column 100 producing a vapor side draw stream. The vapor side draw stream is condensed in the first condenser 114 forming an intermediate product stream. The intermediate product stream is then charged to the dryer 118 producing a purified 1,3-butadiene stream. Compositions of the 1,3-butadiene feedstock, the intermediate product stream, and the purified 1,3-butadiene stream are presented in the Table.

TABLE

| Component | 1,3-Butadiene Feedstock (ppmw) | Intermediate Product Stream (ppmw) | Purified 1,3-Butadiene Stream (ppmw) |
| --- | --- | --- | --- |
| 1,3-butadiene | 999,648.6 | 999,976.7 | 999,982.2 |
| Methanol | 1.5 | 1.5 | 1 |
| Vinyl Acetylene | 1 | 1 | 1 |
| Propadiene | 2 | 2 | 2 |
| Methyl Acetylene | 1 | 1 | 1 |
| Ethyl Acetylene | 1 | 1 | 1 |
| Pentane | 22.1 | 5.4 | 5.4 |
| 1,3-Butadiene Dimer | 69.1 | 0.7 | 0.7 |
| tert-Butyl Catechol | 23.0 | — | — |
| Water | 191.6 | 1 | 1 |
| Oxygen | 26.7 | — | — |
| 1,2-Butadiene | 3.6 | 2.7 | 2.7 |
| Acetaldehyde | 1.8 | 1 | 1 |
| Hydrogen Sulfide | 1 | 1 | 1 |
| Peroxide | 1 | — | — |
| Diethylhydroxylamine | 5 | 5 | — |
| Total | 1,000,000 | 1,000,000 | 1,000,000 |
| Total Impurities | 351 | 23 | 18 |

As presented in the Table, the impurities in the 1,3-butadiene feedstock are reduced from 351 ppmw to 18 ppmw by the inventive purification system, a 95% decrease.

Whereas this invention has been described in terms of the preferred embodiments, reasonable variations and modifications are possible by those skilled in the art. Such modifications are within the scope of the described invention and appended claims.

What is claimed is:

1. A purification process for purifying a 1,3-butadiene feedstock comprising 1,3-butadiene, water, a polymerization inhibitor, and at least one heavy impurity, comprising the steps of:

separating said 1,3-butadiene feedstock, employing a separation column defining a separation zone having an upper portion and a lower portion, into an overhead stream comprising water, a bottoms stream comprising at least one heavy impurity and a polymerization inhibitor, and a vapor side draw stream comprising 1,3-butadiene and residual impurities;

reboiling at least a portion of said bottoms stream to form a boil-up vapor stream and a bottoms residue stream for return of said boil-up vapor stream to said lower portion;

condensing at least a portion of said overhead stream to form a condensed overhead stream;

forming a water phase and a hydrocarbon phase from said condensed overhead stream;

refluxing said hydrocarbon phase to said separation zone;

charging a slip stream of said bottoms residue stream into said overhead stream prior to condensing said at least a portion of said overhead stream;

condensing said vapor side draw stream to form an intermediate product stream; and removing at least a portion of said residual impurities from said intermediate product stream to form a purified 1,3-butadiene stream.

2. A purification process for purifying a 1,3-butadiene feedstock comprising 1,3-butadiene, water, a polymerization inhibitor, and at least one heavy impurity, comprising the steps of:

separating said 1,3-butadiene feedstock, employing a separation column defining a separation zone having an upper portion and a lower portion, into an overhead stream comprising water, a bottoms stream comprising at least one heavy impurity and a polymerization inhibitor, and a vapor side draw stream comprising 1,3-butadiene and residual impurities, wherein said upper portion comprises a first packed bed for separating said vapor side draw stream from said overhead stream, and wherein said lower portion comprises a second packed bed for separating said vapor side draw stream from said bottoms stream;

condensing said vapor side draw stream to form an intermediate product stream; and removing at least a portion of said residual impurities from said intermediate product stream to form a purified 1,3-butadiene stream.

3. A process as recited in claim 2 wherein said first packed bed comprises a plurality of packing elements, and wherein said second packed bed comprises a plurality of packing elements.

4. A purification process for purifying a 1,3-butadiene feedstock comprising 1,3-butadiene, water, a polymerization inhibitor, and at least one heavy impurity, comprising the steps of:

separating said 1,3-butadiene feedstock into an overhead stream comprising water, a bottoms stream comprising at least one heavy impurity and a polymerization inhibitor, and a vapor side draw stream comprising 1,3-butadiene and residual impurities;

condensing said vapor side draw stream to form an intermediate product stream; and removing at least a portion of said residual impurities from said intermediate product stream by passing said intermediate product stream through a dryer to form a purified 1,3-butadiene stream.

5. A system for purifying a 1,3-butadiene feedstock comprising 1,3-butadiene, water, a polymerization inhibitor, and at least one heavy impurity, comprising:

a separation column, defining a separation zone having an upper portion, a medial portion and a lower portion, for separating said 1,3-butadiene feedstock into an overhead stream comprising water, a bottoms stream comprising at least one heavy impurity and a polymerization inhibitor, and a vapor side draw stream comprising 1,3-butadiene and residual impurities;

means for connecting said separation zone in fluid flow communication with a source of said 1,3-butadiene feedstock;

first condensing means in fluid flow communication with said medial portion of said separation zone for condensing said vapor side draw stream to form an intermediate product stream comprising 1,3-butadiene and residual impurities;

means in fluid flow communication with said first condensing means for removing at least a portion of said residual impurities from said intermediate product stream to form a purified 1,3-butadiene stream;

reboiler means in fluid flow communication with said lower portion of said separation zone, for reboiling at least a portion of said bottoms stream to form a boil-up vapor stream and a bottoms residue stream and for returning said boil-up vapor stream to said lower portion of said separation zone;

second condensing means in fluid flow communication with said upper portion of said separation zone for condensing at least a portion of said overhead stream to form a condensed overhead stream, and forming a water phase and a hydrocarbon phase from said condensed overhead stream for return of said hydrocarbon phase to said upper portion of said separation zone; and conduit means in fluid flow communication between said reboiler means and said second condensing means for charging a slip stream of said bottoms residue stream into said overhead stream prior to condensing said at least a portion of said overhead stream.

6. A system as recited in claim 5 wherein said upper portion of said separation zone comprises a first packed bed for separating said vapor side draw stream from said overhead stream, and wherein said lower portion of said separation zone comprises a second packed bed for separating said vapor side draw stream from said bottoms stream.

7. A system as recited in claim 6 wherein said first packed bed comprises a plurality of packing elements, and wherein said second packed bed comprises a plurality of packing elements.

8. A system as recited in claim 5 wherein said means for removing comprises a dryer.

9. A system as recited in claim 5 wherein said means for removing comprises a desiccant dryer.

10. A system for purifying a 1,3-butadiene feedstock comprising 1,3-butadiene, water, a polymerization inhibitor, and at least one heavy impurity, comprising:

a separation column, defining a separation zone having an upper portion, a medial portion and a lower portion, for separating said 1,3-butadiene feedstock into an overhead stream comprising water, a bottoms stream comprising at least one heavy impurity and a polymerization inhibitor, and a vapor side draw stream comprising 1,3-butadiene and residual impurities, wherein said upper portion comprises a first packed bed for separating said vapor side draw stream from said overhead stream and said lower portion comprises a second packed bed for separating said vapor side draw stream from said bottoms stream, and wherein said first packed bed comprises a plurality of packing elements, and wherein said second packed bed comprises a plurality of packing elements;

means for connecting said separation zone in fluid flow communication with a source of said 1,3-butadiene feedstock;

first condensing means in fluid flow communication with said medial portion of said separation zone for condensing said vapor side draw stream to form an intermediate product stream comprising 1,3-butadiene and residual impurities;

a desiccant dryer in fluid flow communication with said first condensing means, for removing at least a portion of said residual impurities from said intermediate product stream to form a purified 1,3-butadiene stream;

reboiler means in fluid flow communication with said lower portion of said separation zone for reboiling at least a portion of said bottoms stream to form a boil-up vapor stream and a bottoms residue stream and for returning said boil-up vapor stream to said lower portion of said separation zone;

second condensing means in fluid flow communication with said upper portion of said separation zone for condensing at least a portion of said overhead stream to form a condensed overhead stream, and forming a water phase and a hydrocarbon phase from said condensed overhead stream for return of said hydrocarbon phase to said upper portion of said separation zone; and conduit means in fluid flow communication between said reboiler means and said second condensing means for charging a slip stream of said bottoms residue stream into said overhead stream prior to condensing said at least a portion of said overhead stream.

* * * * *